United States Patent [19]

Blaser et al.

[11] 4,325,384
[45] Apr. 20, 1982

[54] DIGITALLY CONTROLLED AMPLITUDE REGULATING DEVICE FOR ELECTROCARDIOGRAPHIC SIGNALS

[75] Inventors: Reinhard Blaser, Büdingen; Klaus Olach, Berlin; Max Schaldach, Erlangen, all of Fed. Rep. of Germany

[73] Assignee: BIOTRONIK Mess-und Therapiegeräte GmbH & Co. Ingenieurbüro Berlin, Berlin, Fed. Rep. of Germany

[21] Appl. No.: 101,495

[22] Filed: Dec. 10, 1979

[30] Foreign Application Priority Data

Dec. 9, 1978 [DE] Fed. Rep. of Germany ....... 2853642

[51] Int. Cl.$^3$ .......................... A61B 5/04; A61N 1/36
[52] U.S. Cl. ............................ 128/696; 128/419 PG; 128/708; 128/902
[58] Field of Search ............... 128/696, 702, 704, 706, 128/708, 709, 710, 901, 902, 419 PG

[56] References Cited

U.S. PATENT DOCUMENTS 3,939,824  2/1976  Arneson et al. ................... 128/901

FOREIGN PATENT DOCUMENTS 2113815  10/1971  Fed. Rep. of Germany .
2105692  4/1972  France .

OTHER PUBLICATIONS

Jain et al., "Journal of the Institution of Electronics & Telecommunication Engineers", vol. 23, No. 1, Jan. 1977, pp. 5-6.
Larsen et al., *An Improved Receiver for Baseband Data Communication Using a Digitally Controlled AGC,* Int. J. Electronics, 1977, vol. 43, No. 6, pp. 593-598.
Madkour et al., *A Preprocessing Unit for Wide-Range Measuring Channels,* IEEE Transactions on Industrial Electronics Control Instrumentation, vol. IECI-21, No. 4, Nov. 1974, pp. 230-234.

*Primary Examiner*—William E. Kamm
*Attorney, Agent, or Firm*—Spencer & Kaye

[57] ABSTRACT

A signal processing device composed of: a signal input for receiving an electrocardiographic signal containing a succession of QRS complexes; a signal output; a digitally operating unit having a transmission factor which is variable in discrete steps and connected between the signal input and output for supplying to the signal output a signal containing representations of the QRS complexes contained in the signal received by the signal input, with the relation between the amplitude of the signal at the signal output and the amplitude of the corresponding portions of the signal received by the signal input being proportional to the existing transmission factor of the digitally operating unit; and a transmission factor control unit connected to monitor the signal at the signal output for increasing the transmission factor of the digitally operating unit by one step in response to each appearance at the signal output of a QRS complex representation having a peak value between selected first and second threshold values and for reducing the transmission factor by one step in response to each appearance at the signal output of a QRS complex representation having a peak value greater than a selected third threshold value higher than each of the first and second threshold values.

12 Claims, 3 Drawing Figures

DIGITALLY CONTROLLED AMPLITUDE REGULATING DEVICE FOR ELECTROCARDIOGRAPHIC SIGNALS

BACKGROUND OF THE INVENTION

The present invention relates to a digitally operating device for regulating the amplitude of an electrocardiographic signal.

In a number of biomedical instruments, electrocardiographic signals are used as synchronization signals for electrotherapeutic measures or for the detection or display of signals. The operating conditions fluctuate greatly during operation due, for example, to the inherently unstable nature of the contact provided for derivation of such signals between the transducing electrodes and the patient, and the resulting fluctuating signal amplitudes require a constant adaptation of the amplification in the transmission channel because, on the one hand, if transmission should occur with too much gain, the noise signals contained in the derived signal may be confused with pulses of the QRS complex and, on the other hand, too little amplification will cause the QRS-complexes to be submerged in the noise signals or the occurring amplitude peaks will no longer suffice to actuate the synchronization processes.

The detection of EKG signals is not only made more difficult by their low and changing frequency, but is additionally adversely influenced by occurring interference signals, or artifacts, whose amplitude often exceeds that of the useful signals by a factor of more than one hundred.

It is already known to attempt to deal with these difficulties by effecting an amplitude regulation manually by means of separate operating elements which required additional personnel.

German Offenlegungsschrift [Laid-open Application] No. 2,032,102 discloses a digitally operating circuit arrangement for automatically presetting the gain of an amplifier for electrocardiographic signals in which the input signal is rectified and fed to an integration circuit, one capacitor being charged to the peak value of the positive input signal and one capacitor being charged to the peak value of the negative input signal and being discharged if a lower signal or no signal appears. The thus stored actual value is compared with a desired value and a reciprocal setting member is caused to follow changes in the comparison result in that a counter which receives its clock pulses from a separate oscillator counts upward or downward.

Due to the existing stability conditions, such control devices require integration time constants of the order of magnitude of more than 30 seconds. Such integration constants require either the use of very large capacitances or very low currents, so that difficulties arise in many situations where it is important, for example, that only a small amount of space be occupied by the control devices or that they have a long term stability, such as for use within implantable cardiac pacemakers. Moreover, in such a device the above mentioned high amplitude interference signals, as they are produced, for example, from short-term changes in the contact resistance of the electrodes, generate a regulating effect which considerably reduces the sensitivity of the system and, due to the long regulating time constant, the output amplitude of the QRS complexes returns to the amplitude required, for example, for synchronization purposes, only after a longer period of time.

A number of digitally operating amplitude regulating devices for general application or various specific applications have been described in a multitude of publications. However, such devices will operate at their best only if they are specially adapted to the signals to be processed.

For example, German Offenlegungsschrift No. 2,158,985 discloses a device for regulating the degree of amplification in an alternating voltage amplifier in which, for use in the receiver art, threshold switches are provided which have monostable retriggerable switching states, are set into the astable state when the threshold is exceeded, and maintain this state for a period of time which is slightly longer than the period duration of the fed-in input voltage. The set threshold switch then enables a gating circuit which activates a counter to cause the transmission factor to be reduced in a plurality of steps.

Although in this arrangement no integrating members are used for the input signal, the monostable threshold switch at least contains a timing member including capacitances. Moreover, the regulation operates in a direction toward reducing the amplitude of the output signal. Because of the longer time intervals between successive QRS complexes, the operation performed by this device is not suitable for processing electrocardiographic signals.

SUMMARY OF THE INVENTION

The present invention has for objects to provide an amplitude regulating device for electrocardiographic signals that does not require long time constants, which would require corresponding large capacitances, permits up and down regulation and remains essentially uninfluenced by interference signals while providing an optimum regulating speed. An additional object of the invention is to provide a control device which can be constructed in miniaturized form so that it can be used in cardiac pacemakers and can be included in the signal flow path of such pacemakers.

These and other objects are achieved according to the present invention, by the provision of a signal processing device comprising: a signal input for receiving an electrocardiographic signal containing a succession of QRS complexes; a signal output; digitally operating means having a transmission factor which is variable in discrete steps and connected between the signal input and output for supplying to the signal output a signal containing representations of the QRS complexes contained in the signal received by the signal input, with the relation between the amplitude of the signal at the signal output and the amplitude of the corresponding portions of the signal received by the signal input being proportional to the existing transmission factor of the digitally operating means; and transmission factor control means connected to monitor the signal at the signal output for increasing the transmission factor of the digitally operating means by one step in response to each appearance at the signal output of a QRS complex representation having a peak value between selected first and second threshold values and for reducing the transmission factor by one step in response to each appearance at the signal output of a QRS complex representation having a peak value greater than a selected third threshold value, the second threshold value being higher than the first and lower than the third threshold value.

The present invention is based on recognition that in the described regulation, which is effective only upon the occurrence of a QRS complex since, if the appearing signals do not exceed the first, lower threshold, no contribution is furnished for changing the transmission factor, the required switching states appear in an optimally short time. An integrating average formation of the input signal is not necessary. Since, upon the occurrence of each QRS complex whose maximum amplitude lies outside of limits defined by selected thresholds, a change in amplification is effected by precisely one step, members which store signal states for a period of time so as to enable a counter to generate sufficient pulses to change the transmission factor in many little steps are not required.

According to an advantageous embodiment of the present invention, the moment of the change in the transmission factor is moved to a time period which lies outside the signal components of significance for further signal processing so that a change in the transmission factor even in larger steps will not interfere with the useful signal.

According to another advantageous embodiment of the invention, the danger of the occurrence of instabilities is effectively avoided by the particular dimensioning of the regulating steps taking into consideration resulting change in the output signal.

The stability of the arrangement is further increased in that care is taken that the amplitude regulation does not become effective for the pulse currently being detected but only for successive pulses. This, in particular, prevents feedback.

In connection with use in cardiac pacemakers, it has been found advantageous to change the transmission factor simultaneously with the end of the so-called refractory period following an R pulse so that the trailing edge of the respective pulse generated by the clock pulse generating means can be used as the clock pulse signal.

According to another preferred embodiment, for use in connection with artificial cardiac pacemakers, the transmission factor, i.e. the amplification, is raised to a maximum value if a certain number of pulses, or the pulses during a certain period of time, fall below a given amplitude threshold. This assures that synchronization will reoccur relatively quickly. The high amplitude pulses appearing at the output after the transmission factor has been raised then will definitely reach the thresholds that must be exceeded to cause the amplification to be changed. Additionally, the amplitudes which are still too high when the regulating device adapts itself in the direction toward decreasing amplification, in contradistinction to amplitudes which are too low, already produce a possibly desired synchronization, in subsequently connected devices, to an opposite approximation. Undesired interference signals will not interfere with the operation of artificial cardiac pacemakers even if the gain is relatively high at times because the pacemakers themselves always contain sufficient protective circuits against the influence of such signals on its operation. It is of significance in this connection that the QRS complexes are available in the input signal at sufficient amplitude faster than could be achieved with the conventional rate of change in the transmission factor of such an arrangement.

It is further favorable if, in the case of use in connection with artificial cardiac pacemakers, the stimulation pulses themselves are formed during the measurement. Then the heart signals appearing as a result of the stimulation pulses can also be utilized for the regulation.

DESCRIPTION OF THE PREFERRED EMBODIMENTS

Figure 1:
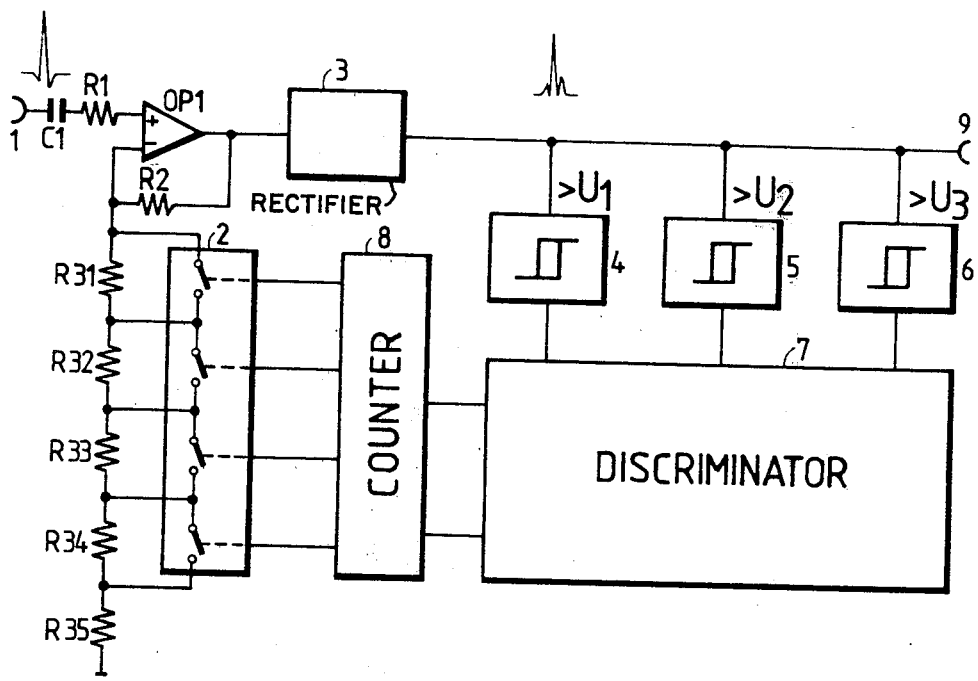
FIG. 1 is a block circuit diagram of a preferred embodiment of an amplitude regulating device according to the invention.

The circuit shown in FIG. 1 includes an input 1 arranged to receive an input signal which forms the measuring value and can be either an EKG signal derived from electrodes on the skin of a patient or a response signal to stimulation pulses as derived from electrodes attached in or at the heart.

The input signal travels through a series path formed by a capacitor C1 and a resistor R1 to the noninverting input of an operational amplifier OP1 whose amplification factor is regulated in accordance with the invention. That amplification factor is determined by a second resistor R2 disposed between the output and inverting input of amplifier OP1 and by the resistance present between the inverting input and ground. The latter resistance is constituted by a series connection of a chain of resistors R31, R32, R33, R34, and R35. The resistors R31 to R34 of the divider chain are each provided with a respective parallel-connected switch, all of the switches being combined in a separate switch module 2. The amplification factor of the operational amplifier can be defined as follows:

$$G = R2 + R31 + \ldots + R35/R31 + \ldots + R35.$$

The output signal of the operational amplifier OP1 is fed to a full wave rectifier 3 at whose output appear at the pulses of the QRS signal with a single polarity.

The rectified signal is fed to three threshold detectors 4, 5 and 6 each of which emits a signal if a given voltage level is exceeded, the schematically indicated hysteresis characteristic of each detector being slight and serving to avoid instabilities. The threshold voltages to be exceeded in the detectors 6, 5, and 4 have a ratio of 40:70:90 with reference to a value of 100 representing the voltage level that can be optimally processed by the subsequent circuits.

A discriminator 7 which will be described in detail below, acts to vary the count state of a counter 8 in dependence on the output signals of the threshold detectors 4 through 6. The count state in counter 8 controls the state of the switches in the switch module 2.

The counter 8 is preferably a binary counter so that with appropriate stepping of the values of resistors R31 to R34 a total of 16 different amplification stages can be set by operating the four switches in the module 2 in corresponding combinations. At the output 9 of the circuit, the rectified QRS signal is available for the stated synchronization purposes. The operation of the discriminator 7 will be explained in detail in connection with the following description of the detailed circuit diagram of an amplitude regulating device according to the present invention as shown in FIG. 2.

Figure 2:
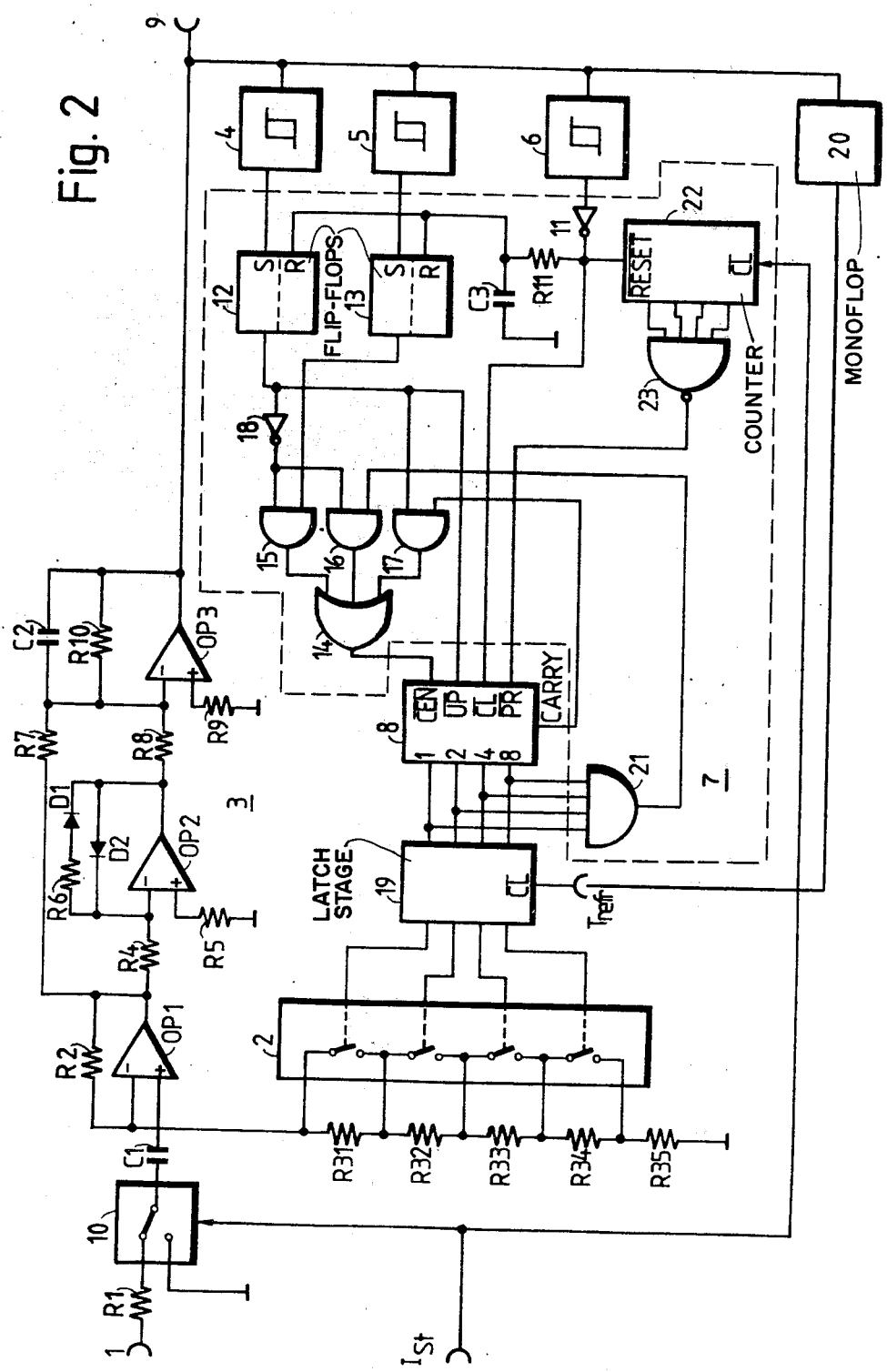
FIG. 2 is a detailed circuit diagram of a preferred form of construction of the embodiment of FIG. 1, and additionally showing a few signal connections to correspond to use in an artificial cardiac pacemaker.

Referring now to FIG. 2, the signal obtained from electrodes attached to the body of a patient reaches, via input 1, resistor R1 which is connected to a clamp switch 10 which is controlled by the signal at input $I_{st}$ in such a manner that the appearance of a selected signal level at that input causes the capacitor C1 connected with the noninverting input of the operational amplifier OP1 to be temporarily placed at a reference potential, e.g. ground. If the present invention is used in cardiac pacemakers and the signals emitted by the heart serve as the regulating parameters, the pacemaker stimulation pulses themselves are thus kept away from the regulating device in the sense of being keyed out, thereby preventing their high amplitude from causing a wrong amplification value to be set. The signal $I_{st}$ is the stimulation output of a conventional pacemaker.

The operational amplifier OP1 and resistors R2 and R31 to R35 are connected in a known manner as a noninverting amplifier. The switch module 2 which influences the gain of the operational amplifier OP1 will be described in detail below.

The output signal from the operational amplifier OP1 reaches the full-wave rectifier 3 which is formed by further operational amplifiers OP2 and OP3. The last-mentioned operational amplifiers form a rectifier circuit with resistors R4 to R10, diodes D1 and D2, and a capacitor C2, all interconnected in a known manner, as shown, so that the output signal of the operational amplifier OP2, which is connected as a half-wave rectifier, is superposed with double amplitude and negative sign on the output signal of the operational amplifier OP1 by means of the operational amplifier OP3 which is connected to operate as linear adder, so that at the output of the operational amplifier OP3, and thus at the output 9 there results as a whole an output signal which corresponds to a full-wave rectification of the QRS signals.

This rectified signal is fed to the threshhold detectors 4, 5 and 6 each of which generates a negative-going signal, or pulse edge, at its output if the rectified signal exceeds its respective threshold value. The association is here such that the detector 4 has the highest threshold value (90%) while the threshold detector 6 emits a signal when the lowest threshold (40%) is passed.

If the rising edge of a pulse appears at the output of the operational amplifier OP3, the threshold value associated with the detector 6 is exceeded first. Exceeding the first threshold, which advantageously is at 40% of the optimum pulse amplitude for which the subsequent circuit connected at output 9 is designed, does not yet cause a switching process to be actuated.

This occurs only if the output voltage of the operational amplifier OP3 again falls below the above-mentioned threshold of detector 6. If, prior to falling below the threshold of detector 6, the pulse at output 9 exceeds the threshold of one or both of detectors 4(90%) and 5 (70%) one or both of the latter detectors are caused to produce a negative-going output voltage which is applied to the setting input S of a respective bistable switching element, here an RS flip-flop, 12 or 13 to set the latter so that after the pulse being monitored passes through a maximum it is determined which thresholds have been exceeded by the pulse. When the trailing edge of the pulse being monitored descends to the lowest amplitude threshold, associated with threshold detector 6, the counter 8, which can count upward and downward, is moved up or down by one value, depending on the threshold reached, or retains its value, respectively.

To achieve this, the trailing edge of the pulse from an inverter 11 connected to the output of detector 6 reaches a clock input $\overline{CL}$ of the counter 8, whereupon a decision is made, based on the signals applied to additional inputs of counter 8, which include count direction input $\overline{UP}$ and gating input $\overline{CEN}$, as to the direction in which the counter counts, or if it counts at all. A signal at the input $\overline{UP}$ switches the counter to downward counting while a signal at the input $\overline{CEN}$ switches on, or enables, the input $\overline{CL}$ and thus permits a change in the counter state.

The identification of the counter inputs with a bar indicates that they respond to negative logic signals or, in the case of the clock input $\overline{CL}$, respond to the trailing edge of a pulse.

The logic circuit composed of an OR gate 14, three AND gates 15, 16 and 17 and an inverter 18 generates the associations to be described below:

If a pulse maximum exceeds only the lowest threshold associated with threshold detector 6, the counter state is advanced by one step by the trailing edge of the pulse applied to the $\overline{CL}$ input from the output of inverter 11 since the counter was not switched to downward counting by a signal at its input $\overline{UP}$ and its $\overline{CL}$ input was not blocked by a signal at input $\overline{CEN}$.

If the amplitude maximum of a pulse in the current QRS complex also reaches and exceeds the amplitude threshold assigned to threshold detector 5, the RS flip-flop 13 is set, i.e. its output goes into the H, or binary "1", state. This signal is then fed via the AND gate 15 whose other input is also in the H state since the output of the flip-flop 12 is in the L, or binary "0", state, and the OR gate 14, to the $\overline{CEN}$ input of the counter 8 so that the $\overline{CL}$ input of the counter 8 is blocked and thus the counter cannot be pulsed by the trailing edge of a pulse coming from the threshold detector 6.

If the amplitude threshold assigned to threshold detector 4 is also exceeded, the flip-flop 12 is set, in addition to flip-flop 13. Since the output of flip-flop 12 is therefore in the H state and the output of inverter 18 is in the L state, the AND gate 15 is blocked and thus the output signal from flip-flop 13 becomes ineffective. The counter 8 is then no longer blocked for the clock pulses coming to its CL input from the threshold detector 6. Since additionally, a signal representing the H, or positive logic state, reaches the input UP of the counter 8 from the output of the flip-flop 12, the counting direction of counter 8 is switched over to downward counting.

The outputs of counter 8 are connected to a latch stage 19 which, timed by a pulse reaching its $\overline{CL}$ input, conducts signals representing the states at the outputs of counter 8, identified with the digital values 1, 2, 4 and 8 to reach the switch module 2. Depending on the momentary state of the counter 8, the resistors 31 to 34, which correspond to the binary numbers having the values $2^0$ to $2^3$, or 1, 2, 4 and 8, respectively, and which have resistance values corresponding to their respective binary values, and for which an output signal is delivered from the associated counter output, are bridged in that the respective parallel switch is closed. The gain of the operational amplifier OP1 is greater, according to the above equation, the lower the total resistance of the divider chain between its inverting input and reference potential or ground. An increase in amplification produced by short-circuiting the associated resistor then corresponds to this value.

Upward counting thus is equivalent to increasing the gain while downward counting leads to a reduction in gain. After a counting process has been performed upon occurrence of the respective trailing edge of an output signal from inverter 11 and in dependence on the state of flip-flops 12 and 13, the flip-flops 12 and 13 are reset to their starting state by signals applied to their R inputs immediately thereafter, with a delay produced by an RC combination of a resistor R11 and capacitor C3.

The transfer of the counter state to the switching module 2 is effected, as already mentioned, via the latch stage 19 which receives through its $\overline{CL}$ input a control pulse that has been delayed by means of a monostable flip-flop, or monoflop, 20. This assures that the amplification of the pulses contained in a QRS complex is not dependent on their own amplitude but is influenced only by the amplitudes of preceding complexes.

For use with cardiac pacemakers, the required monoflop for suppressing pulses during the refractory period $T_{refr}$ following an R peak is provided in any case. The trailing edge of a pulse used for such signal suppression in the pacemaker can therefore be used to advantage to actuate the above-described signal processes.

The logic elements provided additionally take care that the counter 8 cannot count upward beyond its highest state or downward beyond its lowest state, since this would result in jumps in the amplification factor which would interfere with the regulation. If the counter reaches its highest state, i.e., all outputs are at H potential, the output of an AND gate 21 also takes on H potential. Thus the output of the AND gate 16 also changes to the H state if its other input has a corresponding potential. This is precisely the case if the flip-flop 12 is not set, i.e. the counter is not switched to downward counting. Consequently, the clock pulse input $\overline{CL}$ of counter 8 is blocked via the OR gate 14 and the input $\overline{CEN}$.

Correspondingly, further downward counting is prevented if all outputs of the counter are at L potential. In this case, the transfer output CARRY of the counter 8 emits a signal which blocks the counter in a corresponding manner via the AND gate 17 and the OR gate 14 if the flip-flop 12 is set, i.e. the next clock pulse would initiate a further counting process. In this way it is assured that the gain of the operational amplifier OP1 can be changed only within given limits and at small step intervals.

An instability which cannot be excluded with linearly operating regulators can be prevented in a simple way in the regulating device according to the present invention: the differences in the amplitude thresholds associated with the threshold detectors are selected so that they are greater than the change in amplitude of the pulses at the output of the operational amplifier OP3 resulting from a change in gain by one step. Since the absolute amplitudes of the output pulses are kept within narrow limits by the regulation according to the present invention, the amplitude changes resulting from a change in gain also lie within a relatively narrow range so that it is avoided in this way that a change in amplitude of the output pulses as a result of change in gain will immediately produce a renewed change in gain and thus create instability.

Since only one change in gain by one step can occur per pulse when an interference pulse exceeds the highest threshold, independently of the amplitude of that pulse interference peaks even of high amplitude remain essentially without influence on the regulation.

Of particular significance is the case where the amplitudes of the QRS pulses do not exceed the lowermost threshold for a period of time. This may be the case upon the occurrence of a great drop in the available signal amplitude or during idling. It is here important to make available again as soon as possible an EKG signal which is suitable for subsequent evaluation. For synchronization purposes the QRS complexes must have sufficient amplitude. In order to assure, in the case of such an absence of signal, without performing the stepwise increase in gain, that a corresponding output signal is present immediately after the appearance of QRS complexes with evaluatable amplitude, the transmission factor is raised to its maximum if no signal exceeding the lower threshold has appeared for some time.

In order to determine this period of "absence of signals" a further counter 22 is provided which, when used in an artificial demand pacemaker is timed by the artificial stimulation pulses occurring at the asynchronous basic rate. These pulses appear at input $I_{st}$ if no QRS complexes from the heart appear. In other circuit configurations, any suitable clock pulse signal can be used that can represent a time base or the counter 22 can be replaced by a monoflop as the clock pulse generator. The reset input $\overline{RESET}$ through which the inverter 11 is connected with the output of the threshold detector 6 receives a signal for resetting counter 22 each time this threshold detector responds, i.e. a pulse exceeds the associated threshold amplitude.

If the counter 22 reaches a given state, in the illustrated embodiment binary 1111, after a time which is determined by the intended use and generally includes several heartbeats, it sets the counter 8, by means of a NAND gate 23 and counter input $\overline{PR}$, to binary 1111 output state so that the gain of the operational amplifier OP1 is set to its highest value. The counter is always set to the counter state corresponding to the highest gain of operational amplifier OP1 if within a given period of time no pulse appears at the output of the threshold detector 6.

Since the circuit sets itself to the highest gain when there are no pulses of sufficient amplitude, it is assured that typical errors in the derivation of QRS pulses, for example unstable attachment of the electrode used to receive the signals, will cause the synchronization to be reestablished, starting with the highest gain value, in the shortest time since such an absence of signals immediately causes an adaptation to new transmission conditions. Due to the characteristic of pacemaker circuits that they react only to signal pulses which appear at given minimum time intervals, corresponding to the occurrence of QRS pulses in the natural cardiac signal, these circuits are not adversely influenced by interference pulses whose amplitude could possibly have been increased by the increased gain since they usually appear in a different time sequence. If the normal operating state is then reestablished, the occurring heart signals are detected with certainty and the associated transmission factor will quickly return, the subsequent stages generally being better able to process signals which are too high in amplitude than would be the case for signals whose amplitude is too low.

Figure 3:
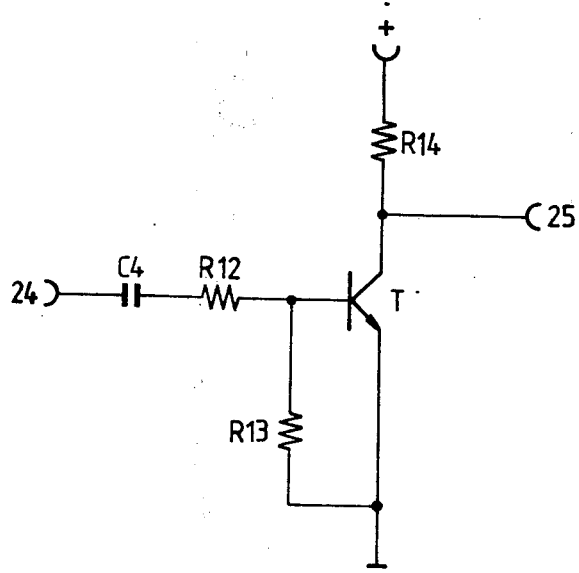
FIG. 3 is a detail view of a component of the circuit of FIG. 2.

FIG. 3 shows a particularly simple embodiment of a threshold detector according to the invention which may be used in a circuit according to FIG. 2. This detector includes an input 24 to which the rectified input signal is applied. The input signal is then conducted via a capacitor C4 which compensates an unchanging direct voltage deviation, the capacitance of capacitor C4 being sufficiently large for the accurate transmission of the signal pulses, to a voltage divider formed of resistors R12 and R13.

The base-emitter path of a transistor T is connected in parallel with the resistor R13. This transistor T becomes conductive if the voltage drop across resistor R13 exceeds the threshold voltage of the transistor, creating a current flow through the collector resistor R14. This results in an abrupt drop in the voltage across the output terminal 25, or a negative-going, or descending, pulse edge whenever the given amplitude threshold of the detector is exceeded, as shown in FIG. 2.

The threshold voltage value can be fixed under consideration of the base-emitter voltage of the transistor by the relationship of the resistors R12/R13. This simple configuration of the threshold detector is of advantage particularly for use in implantable cardiac pacemakers since here the temperature dependence of the threshold voltage of the base-emitter path in the transistor employed cannot have an adverse effect due to the almost constant body temperature of the patient.

When the input voltage drops to a value such that the voltage across resistor R13 is less than the base-emitter threshold voltage of transistor T, the transistor returns to its non-conductive state, creating a positive-going voltage pulse edge at output terminal 25.

The illustrated embodiment constitutes only one possibility for realizing the present invention, the practical embodiment selected depending greatly on the type of components available. For example, if it is desired to realize the invention with the smallest number of generally available components, modifications will be required with respect to the logic gates when CMOS integrated circuit elements are used. The characteristics of the counter components must then also be considered, particularly with respect to their capability to count up and down, and to take on predetermined counter states controlled from separate inputs. There also exists the possibility of realizing the apparatus according to the present invention within the framework of a device which is controlled by a microprocessor. Monoflop 20 is a substitute for the refractory circuit in a conventional pacemaker, which inhibits by its output signal any output action of the pacemaker after a heart beat has been detected. The responsiveness of monoflop 20 to R-peaks of heart signals is indicated by the connection from output 9 to the input of monoflop 20. In pacemaking applications the monoflop may be omitted if there is a direct connection from the output of the refractory circuit to the CL-input of latch-stage 19.

It will be understood that the above description of the present invention is susceptible to various modifications, changes and adaptations, and the same are intended to be comprehended within the meaning and range of equivalents of the appended claims.

What is claimed is:

1. A signal processing device comprising: a signal input for receiving an electrocardiographic signal containing a succession of QRS complexes; a signal output; digitally operating means having a transmission factor which is variable in discrete steps and connected between said signal input and output for supplying to said signal output a signal containing representations of the QRS complexes contained in the signal received by said signal input, with the relation between the amplitude of the signal at said signal output and the amplitude of the corresponding portions of the signal received by said signal input being proportional to the existing transmission factor of said digitally operating means; and transmission factor control means including threshold detector means having associated selected first, second and third threshold values and connected to monitor the signal at said signal output for increasing the transmission factor of said digitally operating means by one step in response to each appearance at said signal output of a QRS complex representation having a peak value between the selected first and second threshold values and for reducing the transmission factor by one step in response to each appearance at said signal output of a QRS complex representation having a peak value greater than the selected third threshold value, said second threshold value being higher than said first threshold value, said third threshold value being higher than said second threshold value, and said first threshold value being higher than the amplitude of the signal at said signal output during intervals between QRS complexes in the electrocardiographic signal.

2. A device as defined in claim 1 wherein: said threshold detector means comprise first, second and third threshold detectors each having an input connected to said signal output, and an output, said first detector means producing, at its output, a first indication when the signal at said signal output rises above said first threshold value and a second indication when the signal at said signal output subsequently drops below said first threshold value, and each of said second and third threshold detectors producing, at its respective output, an indication when the signal at said signal output rises above a respective one of said second and third threshold values; and said transmission factor control means further comprise logic means connected between said outputs of said threshold detectors and said digitally operating means, and including bistable switching elements connected to the outputs of respective ones of said second and third threshold detectors, for influencing the transmission factor upon production of a second indication by said first signal processing means and in a manner determined by the response of said second and third threshold detectors prior to production of that second indication and subsequent to production of the preceding first indication by said first threshold detector.

3. A device as defined in claim 2 wherein said logic means comprise a counter connected to have its count state varied by indications produced at said outputs of said threshold detectors, and said digitally operating means comprise setting elements connected to be set by the count state of said counter for controlling the value of the transmission factor.

4. A device as defined in claim 1 wherein said threshold detector means are set for causing the difference between said second and third threshold values to be greater than the change, at said signal output, in the peak value of a representation of a given QRS complex in the signal received by said signal input, resulting from a transmission factor change of one step.

5. A device as defined in claim 1 wherein the ratio among said first, second and third threshold values is 4:7:9.

6. A device as defined in claim 1 further comprising means connected to said control means for automatically increasing the transmission factor to its maximum value when the signal at said signal output remains below said first threshold value for a period of time corresponding to the period of time within which a plurality of natural QRS complexes should occur.

7. A device as defined in claim 6 in a cardiac pacemaker, wherein said means for automatically increasing the transmission factor comprise a counter connected to count the artificial stimulation pulses produced by the pacemaker, said counter being connected to be reset to a starting count state each time the signal at said signal output exceeds said first threshold value and to increase the transmission factor to its maximum value upon reaching a given count state.

8. A device as defined in claim 1 wherein said transmission factor control means comprise time delay means connected for permitting a change in the transmission factor to be initiated after a QRS representation at said signal output with a delay corresponding to the refractory period associated with a QRS complex.

9. A device as defined in claim 1 in a cardiac pacemaker, wherein said time delay means comprise circuit components provided in said pacemaker for suppressing the emission of artificial stimulation pulses during each refractory period.

10. A device as defined in claim 9 wherein said time delay means comprises means producing a pulse coextensive with each refractory period and means connected to initiate a transmission factor change under control of the trailing edge of each such pulse.

11. A device as defined in claim 1 for use in a cardiac pacemaker which produces artificial stimulation pulses, said device further comprising means connected for blocking the signal transmission path between said signal input and said signal output during the occurrence of each artificial stimulation pulse in order to prevent such pulses from influencing the setting of the transmission factor.

12. A device as defined in claim 1 wherein said transmission factor control means comprise a plurality of threshold detectors each having an input connected to said signal output and arranged to detect a respective one of said threshold values with at least one of said detectors comprising a transistor and a voltage divider connected between the input of said detector and the emitter of said transistor, with an intermediate point of said divider being connected to the base of said transistor, whereby the relation between the base-emitter voltage required for switching the conductive state of said transistor and the associated threshold value voltage corresponds to the dividing ratio of said voltage divider.

* * * * *